United States Patent [19]

Yoshikumi et al.

[11] Patent Number: 4,614,733

[45] Date of Patent: Sep. 30, 1986

[54] POLYSACCHARIDES PHARMACEUTICAL COMPOSITIONS AND THE USE THEREOF

[75] Inventors: Chikao Yoshikumi; Takayoshi Fujii; Masahiko Fujii; Minoru Ohara; Akira Kobayashi, all of Tokyo; Tsuneo Akatsu, Iwaki, all of Japan

[73] Assignee: Kureha Kagaku Kogyo Kabushiki Kaisha, Tokyo, Japan

[21] Appl. No.: 646,433

[22] Filed: Aug. 31, 1984

Related U.S. Application Data

[63] Continuation-in-part of Ser. No. 336,263, Dec. 31, 1981, abandoned, which is a continuation-in-part of Ser. No. 71,287, Aug. 30, 1979, abandoned, which is a continuation-in-part of Ser. No. 870,803, Jan. 19, 1978, abandoned.

[51] Int. Cl.$^4$ .................... A61K 31/715; C08B 37/00
[52] U.S. Cl. ........................................ 514/54; 536/1.1; 536/123
[58] Field of Search ............... 536/1.1, 55.1, 123; 514/54

[56] References Cited

U.S. PATENT DOCUMENTS

| | | | |
|---|---|---|---|
| 4,051,314 | 9/1977 | Ohtsuka et al. | 536/1 |
| 4,140,578 | 2/1979 | Yoshikumi et al. | 536/1 |
| 4,202,885 | 5/1980 | Asano et al. | 536/55.1 |
| 4,202,966 | 5/1980 | Misaki et al. | 536/1 |
| 4,202,969 | 5/1980 | Ueno et al. | 536/55.1 |
| 4,229,570 | 10/1980 | Ueno et al. | 536/55.1 |

OTHER PUBLICATIONS

Ito et al., "Mie Medical Journal", vol. XXII, No. 2–3, 1972–1973, pp. 103–113.; vol. XXIII, 1, pp. 67–79.
Ito, et al., "Chem. Abst.", vol. 80, p. 116284(b), 1974.

*Primary Examiner*—Johnnie R. Brown
*Attorney, Agent, or Firm*—Wegner & Bretschneider

[57] ABSTRACT

Polysaccharides having antitumor and other useful pharmacological activities and a process for preparing such polysaccharides are disclosed. These polysaccharides are characterized by α-bonding of the saccharide component and can be produced from the extracts obtained by the extraction of a basidiomycetous fungus belonging to the genus Coriolus or cultures thereof with an aqueous solvent.

11 Claims, 9 Drawing Figures

POLYSACCHARIDES PHARMACEUTICAL COMPOSITIONS AND THE USE THEREOF

CROSS-REFERENCE TO RELATED APPLICATION

The present application is a continuation-in-part of application Ser. No. 336,263, filed Dec. 31, 1981, now abandoned, which is a continuation-in-part of application Ser. No. 71,287, filed Aug. 30, 1979, now abandoned, which is a continuation-in-part of application Ser. No. 870,803, filed Jan. 19, 1978, now abandoned.

SUMMARY OF THE INVENTION

In a first aspect of the invention, there is provided a polysaccharide having a molecular weight of from 5,000 to 300,000 as determined by ultracentrifugation, giving colour reactions characteristic of saccharides in α-naphthol-sulfuric acid reaction, indole-sulfuric acid reaction, phenol-sulfuric acid reaction, and tryptophane-sulfuric acid reaction, and containing 43.5 to 45.3% of carbon, 5.7 to 6.7% of hydrogen, essentially free of nitrogen and the balance of oxygen, the specific rotation $[\alpha]_D^{25}$ of said polysaccharide being 70 to 180, said polysaccharide showing a specific absorption at 840 cm$^{-1}$ in its infrared absorption spectrum and showing absorptions at 3.7±0.1, 3.8±0.1, 5.0±0.1 and 5.4±0.1 ppm but not absorptions in the range of 4.4 to 4.9 ppm in its nuclear magnetic resonance absorption spectrum, said polysaccharide being soluble in water but insoluble in pyridine, chloroform and hexane, the saccharide units of said polysaccharide being composed principally of D-glucose and the pattern of bonding of said D-glucose in said polysaccharide being entirely α-bonding.

In a second aspect of the invention, there is provided an antitumour agent containing a polysaccharide as an active ingredient, said polysaccharide having a molecular weight of from 5,000 to 300,000 as determined by ultracentrifugation, giving colour reactions characteristic of saccharides in α-naphthol-sulfuric acid reaction, indole-sulfuric acid reaction, phenol-sulfuric acid reaction and tryptophane-sulfuric acid reaction, and containing 43.5 to 45.3% of carbon, 5.7 to 6.7% of hydrogen, essentially free of nitrogen and the balance of oxygen, the specific rotation $[\alpha]_D^{25}$ of said polysaccharide being 70 to 180, said polysaccharide showing a specific absorption at 840 cm$^{-1}$ in its infrared absorption spectrum and showing absorptions at 3.7±0.1, 3.8±0.1, 5.0±0.1 and 5.4±0.1 ppm but no absorptions in the range of 4.4 to 4.9 ppm in its nuclear magnetic resonance absorption spectrum, said polysaccharide being soluble in water but insoluble in pyridine, chloroform and hexane, the saccharide units of said polysaccharide being composed principally of D-glucose and the pattern of bonding of said D-glucose in said polysaccharide being entirely α-bonding.

In a third aspect of the invention, there is provided a pharmaceutical composition in dosage unit form comprising therapeutically effective amount of a polysaccharide as an active ingredient and at least one pharmaceutically acceptable substance selected from the group consisting of galactose, heavy magnesium oxide, starch, monosaccharide, crystalline cellulose, poly(vinyl alcohol), non-ionic surfactant and physiological saline solution, said polysaccharide having a molecular weight of from 5,000 to 300,000 as determined by ultracentrifugation, giving colour reactions characteristic of saccharides in α-naphthol-sulfuric acid reaction, indole-sulfuric acid reaction, phenol-sulfuric acid reaction and tryptophane-sulfuric acid reaction, and containing 43.5 to 45.3% of carbon, 5.7 to 6.7% of hydrogen, essentially free of nitrogen and the balance of oxygen, the specific rotation $[\alpha]_D^{25}$ of said polysaccharide being 70 to 180, said polysaccharide showing a specific absorption at 840 cm$^{-1}$ in its infrared absorption spectrum and showing absorptions at 3.7±0.1, 3.8±0.1, 5.0±0.1 and 5.4±0.1 ppm but no absorptions in the range of 4.4 to 4.9 ppm in its nuclear magnetic resonance absorption spectrum, said polysaccharide being soluble in water but insoluble in pyridine, chloroform and hexane, the saccharide units of said polysaccharide being composed principally of D-glucose and the pattern of bonding of said D-glucose in said polysaccharide being entirely α-bonding.

In a fourth aspect of the invention, there is provided a method of treating mammalian gastro-intestinal cancer which comprises administering to a mammal bearing gastro-intestinal cancer a therapeutically effective amount of antitumour agent containing a polysaccharide as an active ingredient, said polysaccharide having a molecular weight of from 5,000 to 300,000 as determined by ultracentrifugation, giving colour reactions characteristic of saccharides in α-naphthol-sulfuric acid reaction, indole-sulfuric acid reaction, phenol-sulfuric acid reaction and tryptophane-sulfuric acid reaction, and containing 43.5 to 45.3% of carbon, 5.7 to 6.7% of hydrogen, essentially free of nitrogen and the balance of oxygen, the specific rotation $[\alpha]_D^{25}$ of said polysaccharide being 70 to 180, said polysaccharide showing a specific absorption at 840 cm$^{-1}$ in its infrared absorption spectrum and showing absorptions at 3.7±0.1, 3.8±0.1, 5.0±0.1 and 5.4±0.1 ppm but no absorptions in the range of 4.4 to 4.9 ppm in its nuclear magnetic resonance absorption spectrum, said polysaccharide being soluble in water but insoluble in pyridine, chloroform and hexane, the saccharide units of said polysaccharide being composed principally of D-glucose and the pattern of bonding of said D-glucose in said polysaccharide being entirely α-bonding.

In a fifth aspect of the invention, there is provided a polysaccharide containing 43.5 to 45.3% of carbon, 5.7 to 6.7% of hydrogen, essentially free of nitrogen and the balance of oxygen produced by the process comprising the steps of extracting mycelia, fruit bodies of a basidiomycetous fungus belonging to the genus Coriolus or mixtures thereof with an aqueous solvent, saturating the extract solution with ammonium sulfate after removing the low-molecular weight substances with molecular weight of less than 5,000, collecting the resultant precipitate, dissolving said precipitate in water, desalting the thus obtained solution, passing the desalted solution through a column packed with an ion exchanger to adsorb and remove the nitrogenous substance, concentrating the thus obtained solution, and then drying the thus obtained concentrate.

FIELD OF THE INVENTION

This invention relates to polysaccharides, and more particularly to polysaccharides having antitumor and other significant pharmacological activities and characterized by α-bonding of the saccharide component, and the use thereof.

BACKGROUND OF THE INVENTION

Reports have been made on obtention of antitumor substances from various species of basidiomycetous fungi in recent years. These substances show a significant antitumor effect in intraperitoneal administrations, but they prove to be extremely low in antitumor activity when administered orally. Therefore, although these substances could be of much interest for scientific studies, they have little practical utility.

In the course of our studies on the extracts from various species of basidiomycetous fungi and cultures thereof by use of an aqueous solvent, we found that the refined products prepared from the extracts obtained by a basidiomycetous fungus belonging to the genus Coriolus of Polyporaceae or cultures thereof (including the media used for cultivation) have an excellent antitumor activity not only in intraperitoneal administrations but also in oral administrations, and we further carried forward our studies on the active components of these extracts.

We have now succeeded in isolating the active substances having the antitumor activity from the following process: a solution obtained by concentrating a purified aqueous solution of the extract from a fungus of the genus Coriolus or cultures thereof with an aqueous solvent is saturated with ammonium sulfate and the thus-produced precipitate is desalted and then passed through a column packed with an ion exchanger, such as for example a diethylaminoethyl (DEAE) cellulose column, to adsorb and remove the nitrogenous component, and after repeating the operations mentioned above if necessary, the eluate is desalted and dried. We also succeeded in elucidating the characteristic properties of these active substances and attained this invention on the basis of these findings.

BRIEF EXPLANATION OF THE DRAWINGS

The accompanying drawings show the infrared absorption spectra and nuclear magnetic resonance (NMR) absorption spectra of the polysaccharide substances according to this invention, and wherein.

DETAILED DESCRIPTION OF THE INVENTION

Figure 1:
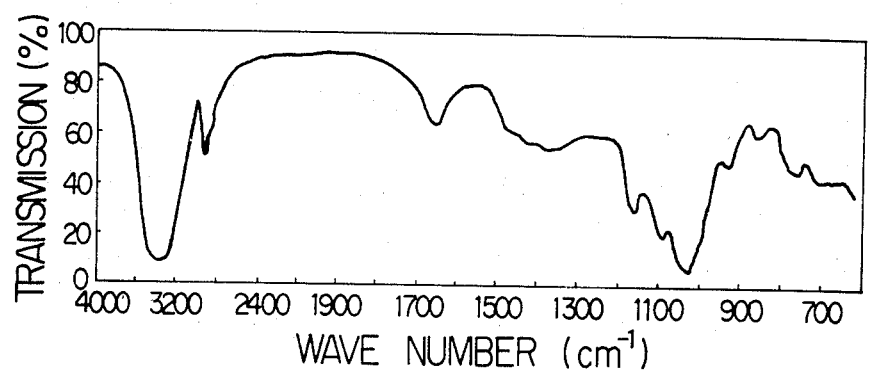
FIGS. 1 to 4 show the infrared absorption spectra of the polysaccharide substances obtained from the fungal species *Coriolus versicolor* (Fr.) Quél. (formerly named *Polystictus versicolor* Fr.) (FIG. 1), *Coriolus hirsutus* (Fr.) Quél. (formerly named *Polystictus hirsutus* Fr.) (FIG. 2), *Coriolus consors* (Berk.) Imaz. (Formerly named *Irpex consors* Berk.) (FIG. 3) and *Coriolus pargamenus* (Fr.) Pat. (formerly named *Polystictus pargamenus* Fr.) (FIG. 4), respectively.
Figure 2:
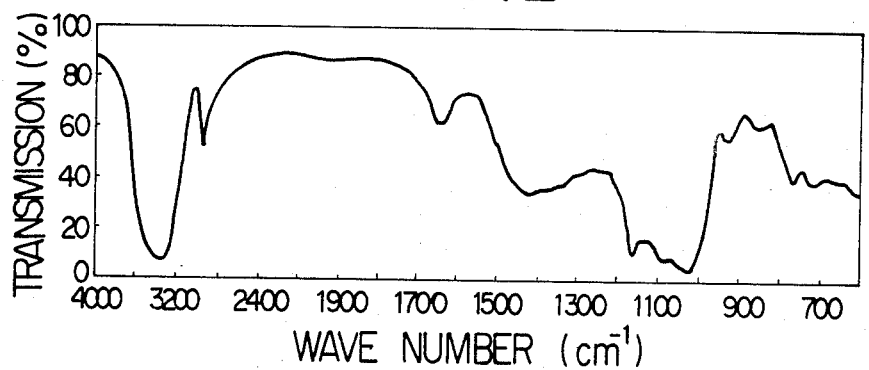
Figure 3:
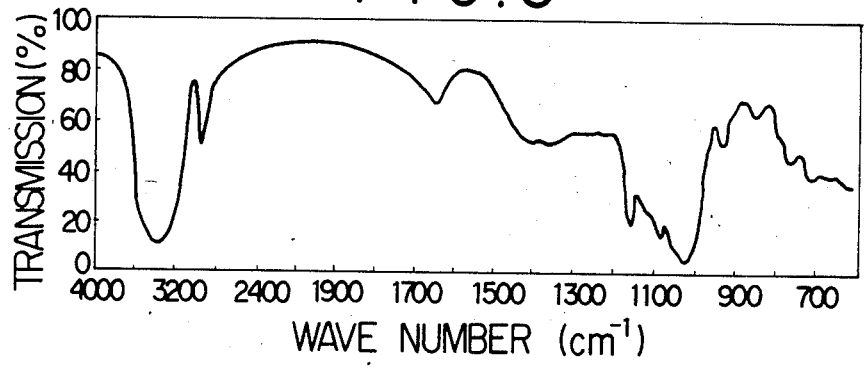
Figure 4:
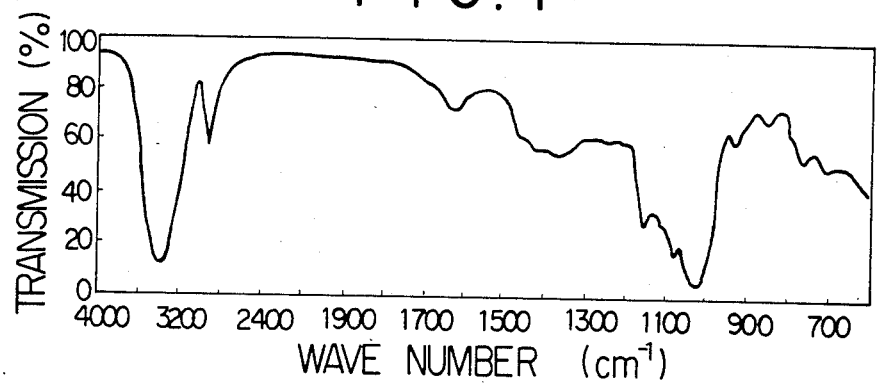
Figure 5:
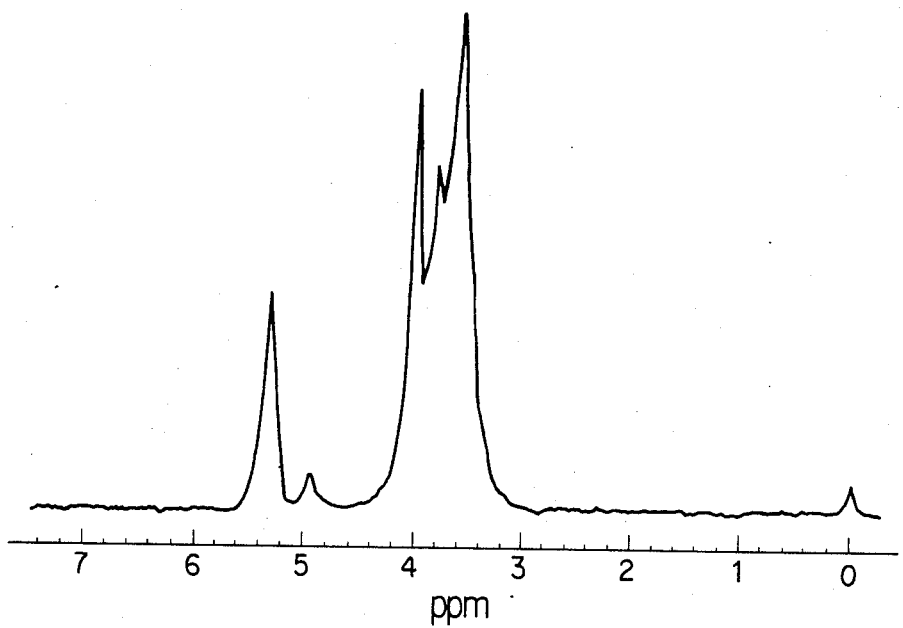
FIGS. 5 to 8 show the NMR absorption spectra of the above-mentioned substances respectively.
Figure 6:
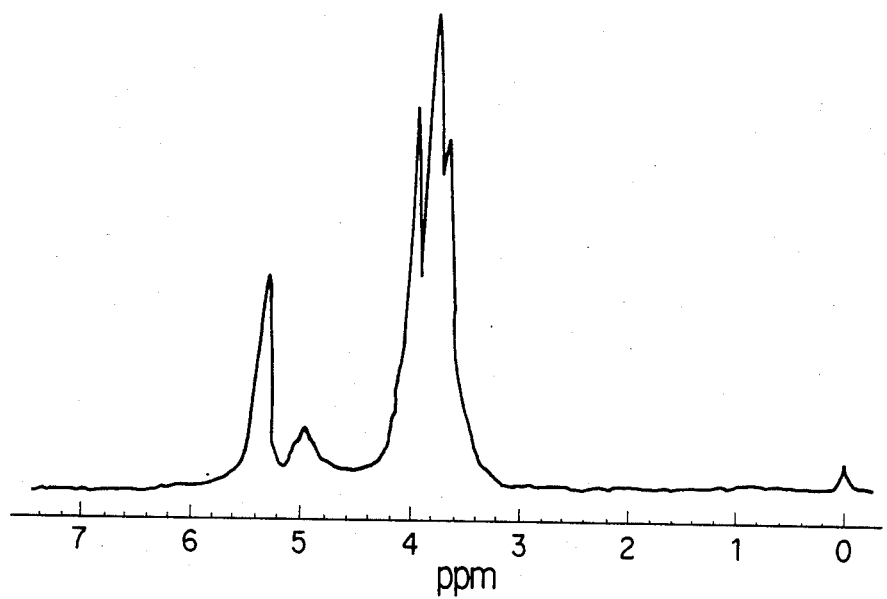
Figure 7:
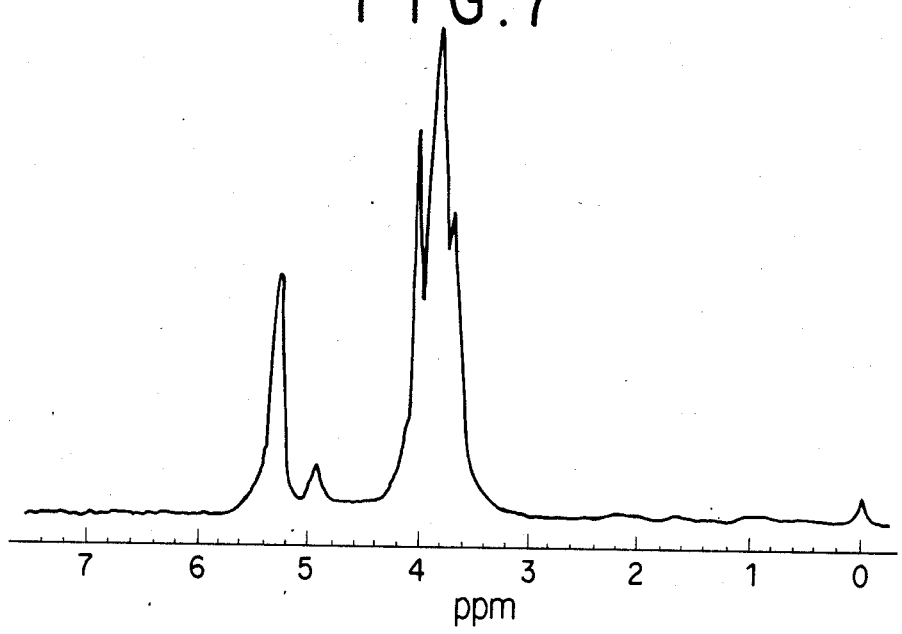
Figure 8:
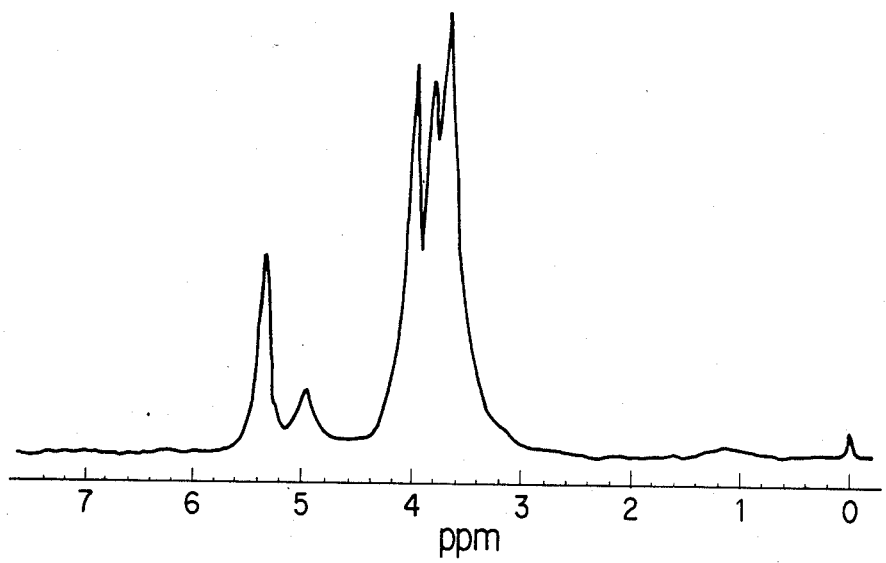

The polysaccharides according to the present invention (hereinafter referred to simply as "present substance") are white powder, tasteless and odorless. The characteristic properties of the present substance are described hereinbelow in due order.

(1) PHYSICAL AND CHEMICAL PROPERTIES

Elementary Analysis

An elementary analysis of the present substances by Yanagimoto Manufacturing Company's Model CHN-CORDER MT-2 Analyzer revealed the following: 43.5 to 45.3% carbon, 5.7 to 6.7% hydrogen, essentially free of nitrogen and the balance of oxygen.

Color Reactions

Color reaction tests were conducted on the aqueous solutions of the present substance to obtain the results shown in Table 1 below.

TABLE 1

| Color reaction | Color | Results |
| --- | --- | --- |
| α-naphtol-sulfuric acid reaction (Molisch reaction) | Purple | Saccharides |
| Indole-sulfuric acid reaction (Dische reaction) | Brown | Saccharides |
| Anthrone-sulfuric acid reaction | Greenish blue | Saccharides |
| Phenol-sulfuric acid reaction | Brown | Saccharides |
| Tryptophane-sulfuric acid reaction | Purplish brown | Saccharides |

It is apparent from the above-shown color reaction test results that the present substance contains saccharides.

pH Value 1 g of the present substance was dissolved in 100 ml of water and the pH value of the solution was measured by using HITACHI-HORIBA Manufacturing Company's M-5 pH Meter. It was within the range of 6.5 to 7.2.

Specific rotatory power

A 0.25% aqueous solution of the present substance was prepared and its optical rotation was measured by using Yanagimoto Manufacturing Company's YANACO OR-50, and the specific rotatory power $[\alpha]_D^{25}$ was determined therefrom. It was within the range of $+70$ to $+180$.

Molecular Weight

The molecular weight of the present substance, as measured by an ultracentrifugal method, was within the range of 5,000 to 300,000, and the average molecular weight was within the range of 10,000 to 100,000. The values obtained according to the other measuring methods, such as fractionating by ultrafiltration, also pointed to the range of 10,000 to 100,000. Therefore, it may be supposed that the average molecular weight of the present substance is within the range of 10,000 to 100,000. The measurement was made by using SPINCO-E Ultracentrifuge.

Solubility

The present substance is well soluble in water but insoluble in pyridine, chloroform, benzene and hexane.

Infrared Absorption Spectrum

Infrared absorption spectra of the present substance as measured according to the potassium bromide tablet method are shown in FIGS. 1 to 4 of the accompanying drawings. No significant difference was noted between the specimens. The spectrum showed absorptions at 3600 to 3200 cm$^{-1}$, 2920 to 2900 cm$^{-1}$, 1660 to 1610 cm$^{-1}$, 1460 cm$^{-1}$, 1410 cm$^{-1}$, 1360 cm$^{-1}$, 1230 cm$^{-1}$, 1150 cm$^{-1}$, 1080 cm$^{-1}$, 1060 to 990 cm$^{-1}$, 925 cm$^{-1}$, 840 cm$^{-1}$, 755 cm$^{-1}$ and 705 cm$^{-1}$. The broad absorption band in a range of from 3600 to 3200 cm$^{-1}$ as seen in FIGS. 1 to 4 is considered to be attributable to νOH's which are hydrogen-bonded at various degrees. This can be assumed, for example, from the fact that this broad absorption band vanishes when the hydroxy groups in the saccharide portion of specimen are O-methylated. Another broad absorption in a range of from 1200 to 1000 cm$^{-1}$ may be attributed to the unsymmetric stretching vibration of C—O—C linkage in the pyranose rings in the saccharide portion. Absorption at 840 cm$^{-1}$ is ascribable to α-bonding of saccharides. This absorption is indicative of α-bonding of saccharides in the present substance. The measurements were made by using Nippon Bunkosha's DS-701 Spectrum Analyzer.

Proton Nuclear Magnetic Resonance (NMR) Absorption Spectrum

The NMR (100 MHz) absorption spectrum of the present substance was measured by using Varian's Model A spectrum Analyzer. Heavy water was used as the solvent while adopting sodium 2,2-dimethyl-2-silanopentane-5-sulfonate (D.S.S.) as the internal standard. The results are shown in FIGS. 5 to 8.

Figure 9:
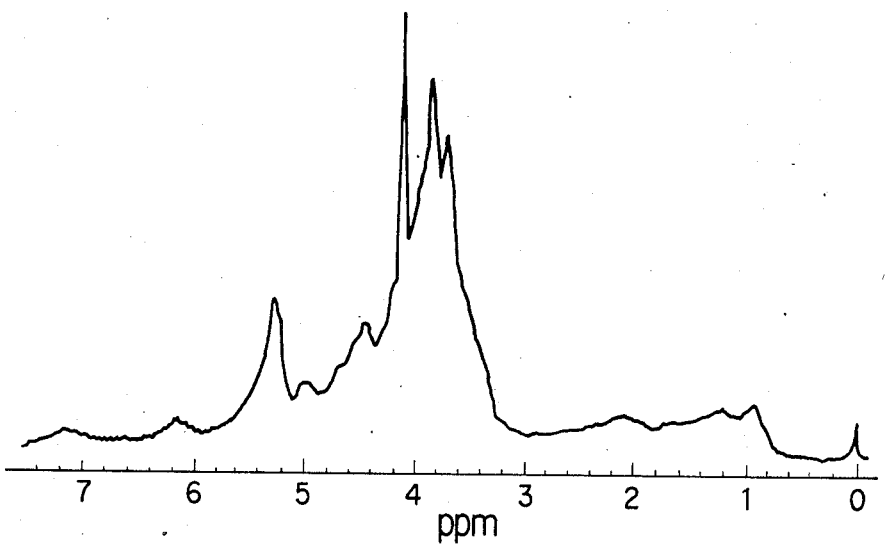
FIG. 9 shows the NMR spectrum of one of the known polysaccharides disclosed in British Pat. No. 1,331,513, which is treated as the control in the present invention.

Absorption at 2.5 to 6.0 ppm in FIGS. 5 to 8 is attributable to protons in the saccharide portion while absorption at 5.0 ppm is ascribable to α-(1→6) bonding and that at 5.4 ppm to α-(1→4) and α-(1→3) bonding. By way of control, there is shown in FIG. 9 an NMR absorption spectrum of a known product obtained by filtering and sterilizing under pressure and then spray-drying the extract obtained from a basidiomycetous fungus belonging to the genus Coriolus of the family Polyporaceae, the product being disclosed in British Pat. No. 1,331,513. The most prominent difference between the above-mentioned known product and the present substance as noticed from the comparison of the absorption spectra shown in FIGS. 5 to 8 and that shown in FIG. 9 is that, in the case of the present substance, although there is observed an absorption at 4.9 to 6.0 ppm originating from α-bonding, no absorption is seen in the range of 4.4 to 4.9 ppm attributable to β-bonding. This indicates that the saccharide components of the present substance are all α-bonded. As regards the quantitative measurement of the mode of bonding of the saccharides in the present substance, a certain assumption may be made from α-(1→6) bonding observed at 5.0 ppm and α-(1→4) and α-(1→3) bonding observed at 5.4 ppm, but since α-(1→4) bonding and α-(1→3) bonding overlaps at 5.4 ppm, the accurate quantitative measurement of the respective bonds is difficult. Further, since the present substance has a branched structure, the minute structural elucidation of the substance must resort to the methylation method described below.

(2) STRUCTURAL CHARACTERISTICS

In order to identify the saccharide component in the saccharide portion of the present substance, 10 mg of the present substance were mixed with a 3% hydrochloric acid solution in methanol for methanolysis at 100° C. for 16 hours and then, after trimethylsilation according to an ordinary method, subjected to gas chromatography. The results showed that glucose is predominent and other saccharides such as mannose, galactose, xylose and fucose are very scarce.

In order to ascertain the form (either D form or L form) of glucose which is the principal saccharide component in the saccharide portion of the present substance, glucose crystals were separated from the hydrolyzate of the present substance. It was found that the thus separated glucose had a melting point of 143 to 145° C. and showed no drop of melting point when mixed and melted with a standard D-glucose preparation. These results identified the glucose in the saccharide portion of the present substance as D-glucose.

Then the position of glycosidic linkage was determined in the following way. The linkage patterns of $G^1\rightarrow$ ($G^1\rightarrow$ means glucose structure skeleton), $\rightarrow^4G^1\rightarrow$, $\rightarrow^4G_3^1\rightarrow$, $\rightarrow^4G_6^1\rightarrow$, $\rightarrow^3G^1\rightarrow$ and $\rightarrow^3G_6^1\rightarrow$ were confirmed from analysis of the monosaccharides obtained according to the periodate oxidation method or Smith's decomposition method, and their ratios were determined by the methylation experiments according to Haworth's method. As for identification, the saccharides obtained by hydrolysis of the methylation products were identified by gas chromatography as alditolacetate and methyl glucoside, and further, the individual hydrolyzates were isolated by column liquid chromatography and then crystallized or converted into crystalline derivatives for confirmation.

The molar ratios of the respective linkages in the present substance are shown in Table 2 below by indexing the molar ratio of $G^1\rightarrow$ linkage as 1. The molar ratios in Table 2 were determined from the area ratios on the gas chromatograph of alditol-acetate.

TABLE 2

| Hydrolyzates of methylated sugars | Linkage | Molar ratio |
|---|---|---|
| 2,3,4,6-tetra-O—methyl-G | $G^1\rightarrow$ | 1 |
| 2,3,6-tri-O—methyl-G | $\rightarrow^4G^1\rightarrow$ | 3.5 to 8.5 |
| 2,3-di-O—methyl-G | $\rightarrow^4G_6^1\rightarrow$ | 0.5 to 2 |
| 2,6-di-O—methyl-G | $\rightarrow^4G^1\rightarrow$ | 0.1 to 2.5 |
| 2,4,6-tri-O—methyl-G | $\rightarrow^3G^1\rightarrow$ | 2 or less |
| 2,4-di-O—methyl-G | $\rightarrow^3G_6^1\rightarrow$ | 0.8 or less |

According to Table 2, it is considered that the polysaccharide portion of the present substance is mostly composed of α-(1→4) bonds, but there also exist α-(1→3) bonds and numerous branches in the polysaccharide portion. This may be construed as indicating that the present substance is of a structure where side chains are bonded to the main chains of glucan of α-(1→4) bonding, with the glucan portions of α-(1→3) bonding of the similar structure being scattered therein.

Now the process for the preparation of the polysaccharides according to this invention will be described. The polysaccharides of the present invention, as described above, are extracted from the fruit bodies or mycelia of a natural- or artificially-cultured basidiomycetous fungus belonging to the genus Coriolus of the family Polyporaceae of the order Aphyllophorales.

For identification of the fungi used in the present invention, we refer to "COLOURED ILLUSTRATIONS OF FUNGI OF JAPAN" by Rokuya Imazeki and Tsuguo Hongo (Hoikusha Press) and "FUNGI OF JAPAN" by Seiya Ito (Yokendo Press). This publication discloses the starting material used for the extraction of the polysaccharide substances of the present invention, that is, the basidiomycetous fungi from which the cultures for the extraction are obtained, i.e., species belonging to the genus Coriolus, such as for example *Coriolus consors* (Berk.) Imaz. *Coriolus versicolor* (Fr.) Quél. *Coriolus hirsutus* (Fr.) Quél. and *Coriolus pargamenus* (Fr.) Pat. These fungi are deposited, under the Deposit Nos. shown in the following table, in the Fermentation Research Institute (F.R.I.) of Agency of Industrial Science and Technology, a depository designated by the Japanese Government.

TABLE 3

| No. | Species | Strain | Deposit No. |
|---|---|---|---|
| 1 | Coriolus consors (Berk.) Imaz. | CM-166 | FERM-P No. 988 |
| 2 | Coriolus versicolor (Fr.) Quel. | CM-103 | FERM-P No.2414 |
| 3 | " | CM-104 | FERM-P No.2415 |
| 4 | " | CM-105 | FERM-P No.2416 |
| 5 | " | CM-106 | FERM-P No.2417 |
| 6 | " | CM-107 | FERM-P No.2418 |
| 7 | " | CM-108 | FERM-P No.2419 |
| 8 | " | CM-109 | FERM-P No.2420 |
| 9 | " | CM-110 | FERM-P No.2421 |
| 10 | " | CM-111 | FERM-P No.2422 |
| 11 | " | CM-112 | FERM-P No.2423 |
| 12 | " | CM-113 | FERM-P No.2424 |
| 13 | " | CM-114 | FERM-P No.2425 |
| 14 | " | CM-115 | FERM-P No.2426 |
| 15 | Coriolus hirsutus (Fr.) Quel. | CM-151 | FERM-P No.2711 |
| 16 | Coriolus pargamenus (Fr.) Pat. | CM-161 | FERM-P No.2712 |

As mentioned above, the starting material used for the extraction of the polysaccharide substance of the present invention may be either natural fruit bodies and/or mycelia, or atritificially-cultured fruit bodies and/or mycelia, and the starting material is subjected to the step of extraction, but if desired it may be preserved after a suitable drying treatment such as air drying or freeze-drying for use later on. It is preferable to pulverize the material before subjecting it to the extraction step since such treatment raises extraction efficiency. The extraction of the material is performed by using an aqueous solvent. The aqueous solvent used here is water or an aqueous solution of a small quantity, for example about 10% or less, of an organic solvent, acid or base which is soluble in water. Preferred examples of organic solvent used for the purpose are methanol, ethanol and isopropyl alcohol. The acid used here may be hydrochloric acid, sulfuric acid, acetic acid or the like, and the base may be ammonia, caustic soda, caustic potash, sodium carbonate or the like. Among these aqueous solvents, most preferred are water and a dilute alkali solution, particularly an aqueous solution of caustic soda or caustic potash of a normality within the range of 0.005 to 2N. The extraction is carried out by using the aqueous solvent, such as mentioned above, in an amount 5 to 200 times the quantity (on dry basis) of the cultured material to be extracted, at a temperature of usually 50° to 100° C. for a period of 20 minutes to 20 hours. An extraction temperature of lower than 50° C. results in a poor extraction efficiency, so that it is generally preferred to perform the extraction at a temperature within the range of 80° to 98° C. The number of runs of extraction is usually less than 10, preferably 3 to 8. It is preferable for the reason of preventing decomposition of active substances to confine the total period of extraction to less than 20 hours regardless of the number of runs of extraction. On the other hand, from the viewpoint of extraction efficiency, it is preferable to perform the extraction for more than one hour. The aqueous solvent used for the extraction is selected from the group stated above, but it is not essential to use only one of the solvents; in some cases, even better results are provided by using two or more kinds of the solvents in combination, for example a combination of water and a dilute alkali solution.

The most preferable mode of extraction in the present invention is a multi-stage extraction by the use of a series of aqueous dilute alkali solutions or by the use of water and the series of aqueous dilute alkali solutions, the concentration (or the normality) of the aqueous dilute alkali solution used in a certain stage of extraction being higher than that of the aqueous dilute alkali solution used in the preceding stage of extraction. Such a mode of extraction results in a striking improvement of the efficiency of extraction. Although the reason for such an improved efficiency of extraction has not been elucidated, it is presumed that, in such a mode of extraction, not only the mere elution of the soluble substance in the material subjected to extraction but also a mild degradation of them aterial is caused by the higher normality of the alkali, thereby facilitating the extraction of the solubilized substance formed by the mild degradation. It is thus considered that, according to such multi-stage extraction, the degradation occurs to facilitate the extraction of the active substance solubilized in each stage with the higher normality of the alkali than the preceding stage.

On the other hand, in the case where an aqueous alkali solution of a relatively high normality is used from the beginning of the extraction, the yield of the object substance in the posterior stage is very low. The fact is considered to be due to the following reason: the fraction of the material to be extracted in the stage has been degraded excessively by the relatively high normality of the alkali in the preceding stage, resulting in the formation of the too-much degraded substance of low molecular weight rather than the preferable polysaccharides of high molecular weight.

The liquid extract obtained by the above-mentioned extraction process is neutralized according to an ordinary method by using an alkali in the case of acid extraction and by using an acid in the case of alkali extraction, and the thus neutralized liquid extract is then subjected to a refining treatment. The refining treatment practiced here is intended to get rid of the low-molecular-weight substances (with molecular weight of less than 5,000) contained in the extract, and such treatment may be accomplished by salting-out, dialysis, ultrafiltration, reverse osmosis, gel filtration or sedimentation by use of an organic solvent, such techniques being employed either singly or in combination. From the standpoint of engineering, it is preferred to employ ultrafiltration, which is a membrane separation method under pressure, or reverse osmosis either singly or in combination, but in some cases, such refining treatment may be practiced after previously performing a salting-out treatment on the extract. The dialysis for the refining treatment is usually carried out by using a cellophane membrane, collodion diaphragm or cellulose membrane. The salting-out agent used for the salting-out treatment may be ammonium sulfate, common salt, potassium chloride, barium carbonate or the like, but ammonium sulfate is most preferred. In case of having practiced the salting-out treatment, it is followed by dialysis, ultrafiltration, gel filtration, reverse osmosis or sedimentation. Gel filtration is performed by using a column packed with dextran or polyacrylamide gel. In this case, there is usually used a filler sold by the registered tradename of Cephadex Biogel. Both ultrafiltration and reverse osmosis belong to a fractionating method practiced by using a membrane under pressure, usually 0.5 to 5 kg/cm² in the former and 20 to 35 kg/cm² in the latter. In case of employing sedimentation, an organic solvent such as methanol, ethanol, isopropanol and acetone is generally used. If need be, an ion-exchange treatment may be practiced concurrently with the operation mentioned above.

The above-mentioned refining treatment in the present invention is essential for the reason that the low-molecular-weight fraction, or the substance with molecular weight of less than 5,000, released from the extract by the treatment shows almost no inhibitory activity against Sarcoma-180 solid type tumors in intraperitoneal administration on mice, and also such fraction has slight bitterness and odor. Thus, the presence of such low-molecular fraction is undesirable from the viewpoint of pharmaceutical potency of the object polysaccharide substance of the present invention.

The thus refined liquid obtained by the above-mentioned refining treatment is adjusted to contain the present substance in a concentration of 1 to 20% by weight, preferably 3 to 10%, and then saturated with ammonium sulfate, and the resultant precipitate is collected. This precipitate is then dissolved in water and subjected to dialysis, ultrafiltration or reverse osmosis, and after adjusting its concentration to 3 to 10%, this solution is passed through a diethylaminoethyl (DEAE) cellulose column to adsorb and remove the nitrogenous component, and after repeating the above-mentioned operation if so required, the obtained eluate is concentrated and dried. There is consequently obtained the object polysaccharide substance as a white, tasteless and odorless powder.

We will now describe the antitumor activity of the polysaccharide substance of the present invention while showing the results of various animal tests.

ACUTE MAMMALIAN TOXICITY

Acute toxicity to mice and rats:

The mice used in this test were of ICR-JCL strain, 4 to 5 weeks old, each weighing 21 to 24 g, and the rats were of Donryu strain, 4 to 5 weeks old, each weighing 100 to 150 g. The present substance was administered via each of the following four routes: intravenous, subcutaneous, intraperitoneal and oral. Observations were made on general symptoms, death and body weight for 7 days after administration of the substance, and after completion of this observation period, the animals were killed and autopsied. The results are shown in Table 4 below. No death was caused by administration of the substance even with the maximum dosage in both rats and mice, and accordingly it was practically impossible to calculate the numerical values of $LD_{50}$.

TABLE 4

| Species of animal | Route of administration | $LD_{50}$ (mg/kg) Female | $LD_{50}$ (mg/kg) Male |
|---|---|---|---|
| Mice | Intravenous | >1,300 | >1,300 |
| | Subcutaneous | >5,000 | >5,000 |
| | Intraperitoneal | >5,000 | >5,000 |
| | Oral | >20,000 | >20,000 |
| Rats | Intravenous | >600 | >600 |
| | Subcutaneous | >5,000 | >5,000 |
| | Intraperitoneal | >5,000 | >5,000 |

TABLE 4-continued

| Species of animal | Route of administration | $LD_{50}$ (mg/kg) Female | $LD_{50}$ (mg/kg) Male |
|---|---|---|---|
| | Oral | >20,000 | >20,000 |

ANTITUMOR ACTIVITY

The antitumor activity of the present substance was examined according to the two ordinary methods outlined below.

(1) Against the transplanted sarcoma-180 solid tumor cells

Sarcoma-180 solid tumor cells were inoculated into the peritoneal cavity of each of ICR-JCL mice, and after a 7-day period in which sufficient growth of the tumor cells took place, $10^6$ cells were inoculated under axially skin of each of another ten mice. The administration of the present substance to each of the thus treated mice was started after 24 hours of the inoculation, as a solution in an aqueous physiological saline solution. In the case of intraperitoneal administration, the substance was given once every other day at a daily dose rate of 10 mg/kg (0.2 ml of the solution/20 g body weight) for a total administration of ten times, and in the case of oral administration, once every day at a daily dose rate of 1,000 mg/kg (0.2 ml of the solution/20 g body weight) for a total administration of twenty times. 25 days after inoculation, the tumors in each mouse were enucleated, and the tumor growth inhibition rate was calculated from the average weight of tumors in the administered groups and the average weight of tumors in the control group. The results are shown in Table 5 below. The test results obtained from the above-mentioned measurements indicate excellent antitumor effect of the present substance not only in intraperitoneal administration but also in oral administration. The specimens of the present substance used in the test were prepared from the extracts of the cultures of the fungal species, respectively shown in Table 5 below.

TABLE 5

In vivo antitumor effect against transplanted sarcoma-180 cells in mice

| Fungal species | Strain F.R.I. Dep. FERM-P No. | Route of inoculation - administration | Dose (mg/kg × nos. of times of administration) | Tumor growth inhibition rate (%) |
|---|---|---|---|---|
| Coriolus consors (Berk.) Imaz. | 988 | SC - ip | 10 × 10 | 90 |
| | | SC - po | 1000 × 20 | 55 |
| Coriolus versicolor (Fr.) Quel. | 2414 | SC - ip | 10 × 10 | 95 |
| | | SC - po | 1000 × 20 | 70 |
| Coriolus hirsutus (Fr.) Quel. | 2711 | SC - ip | 10 × 10 | 92 |
| | | SC - po | 1000 × 20 | 60 |
| Coriolus pargamenus (Fr.) Pat. | 2712 | SC - ip | 10 × 10 | 90 |
| | | SC - po | 1000 × 20 | 60 |

(2) Against the transplanted Ehrlich (ascites) tumor cells:

Ehrlich tumor cells were inoculated to the peritoneal cavity of each of ICR-JCL mice, and after a 7-day period in which the thus transplanted fumor cells grew sufficiently, the proliferated tumour cells were collected from the ascites of the mice, and the cells were inoculated under the auxially skins of each of another 10 mice. The administration of the present substance to each of the thus treated mice was started after 24 hours of the inoculation, as a solution in an aqueous physiological saline solution. In the case of intraperitoneal administration, the substance was given once every other day at a daily dose rate of 5, 10 or 20 mg/kg body weight for a total administration of 10 times, and in the case of oral administration, the substance was given every day at a daily dose rate of 100, 600 or 1,000 mg/kg body weight for a total administration of 20 times. The tumors in each of the mice were enucleated after 25 days of the inoculation, and the tumor growth inhibition rate was calculated from the average weight of tumors in the administered group and that in the control group (inoculated but not administered with the present substance). The results are shown in Table 6. As are seen in Table 6, the present substance showed an excellent antitumor activity not only in intraperitoneal administration but also in oral administration. The specimens of the present substance used in the test were prepared in Examples shown in Table 6.

TABLE 6

In vivo antitumor effect against transplanted Ehrlich tumor cells
Rate of inhibition of tumor growth (%)
Tumor growth inhibition rate (%)

| Substance obtained in | Example 1 | Example 2 | | |
|---|---|---|---|---|
| Substance Number | — | 2-1 | 2-2 | 2-3 |
| Route of admin. (1) intraperitoneal (every other day, in total, ten times) dose rate (mg/kg)/day | | | | |
| 5 | 93.3 | 94.5 | 94.9 | 91.3 |
| 10 | 96.9 | 94.1 | 94.5 | 90.6 |
| 50 | 98.4 | 95.9 | 97.1 | 97.6 |
| (2) oral (every day, in total, twenty times) dose rate (mg/kg)/day | | | | |
| 100 | 62.8 | 65.8 | 63.7 | 62.8 |
| 600 | 67.4 | 64.0 | 70.5 | 68.2 |
| 1000 | 74.2 | 70.8 | 71.6 | 70.5 |

Notes:
Transplanted cells: Ehrlich (ascites) tumor at $2 \times 10^6$/animal
Animals: female ICR-JCL mice of 5th week after birth, ten mice constituting a group.

TABLE 7

| Item | Prepared in Example 1 | Substance Prepared in Example 2 | | |
|---|---|---|---|---|
| | | Substance No.2-1 | Substance No.2-2 | Substance No.2-3 |
| F.R.I. Deposit No. FERM-P | No. 2414 | No. 988 | No. 2712 | No. 2711 |
| Strain No. | CM-103 | CM-166 | CM-161 | CM-151 |
| Extraction method | Hot water-alkali | Alkali | Alkali | Alkali |
| Molecular weight ($\times 10^4$) | 0.7–28 | 0.5–26 | 1–20 | 0.5–30 |
| Average mol. wt. ($\times 10^4$) | 7.0 | 9.0 | 8.2 | 9.5 |
| Color reaction (saccharide) | | | | |
| α-naphthol-sulfuric acid reaction | purple | Same as left | Same as left | Same as left |
| Indol-sul. acid reaction | Brown | Same as left | Same as left | Same as left |
| Anthrone-sul. acid reaction | Greenish blue | Same as left | Same as left | Same as left |
| Phenol-sul. acid reaction | Brown | Same as left | Same as left | Same as left |
| Tryptophane-sul. acid reaction | Purplish brown | Same as left | Same as left | Same as left |
| pH | 6.8 | 6.6 | 7.0 | 6.9 |
| Specific rotation $[\alpha]_D^{25}$ | +170 | +150 | +100 | +160 |
| Elementary analytical data | | | | |
| C(%) | 44.49 | 43.68 | 43.98 | 45.02 |
| H(%) | 6.21 | 5.99 | 6.39 | 6.53 |
| N(%) | 0 | 0 | 0 | 0 |
| NMR absorption spectra Absorption positions[1] (ppm) | | | | |
| 0.9–2.0 ppm | Absent | Absent | Absent | Absent |
| 3.6–3.9 ppm | Present | Present | Present | Present |
| 5.0 ± 0.1 ppm | " | " | " | " |
| 5.4 ± 0.1 ppm | " | " | " | " |
| Main sugar constituent | D-glucose | D-glucose | D-glucose | D-glucose |
| Infrared absorption spectra | | | | |
| 3600–3200 cm$^{-1}$ | Present | Present | Present | Present |
| 2920–2900 cm$^{-1}$ | " | " | " | " |
| 1660–1610 cm$^{-1}$ | " | " | " | " |
| 1460,1410,1360,1230 cm$^{-1}$ | " | " | " | " |
| 890 cm$^{-1}$ | Absent | Absent | Absent | Absent |
| 840 cm$^{-1}$ | Present | Present | Present | Present |
| Saccharide analysis (pattern of bonding) | | | | |
| →$^4$G$^1$→ | 5.5 | 3.9 | 6.0 | 6.8 |
| →$^3$G$^1$→ | 1.0 | 1.5 | 1.9 | 1.5 |
| →$^4$G$^1_6$→ | 0.9 | 1.2 | 1.0 | 1.3 |
| →$^4$G$^1_3$→ | 2.1 | 0.5 | 1.2 | 0.4 |

TABLE 7-continued

| | | Substance | | | |
|---|---|---|---|---|---|
| | | Prepared in Example 1 | Prepared in Example 2 | | |
| Item | | — | Substance No.2-1 | Substance No.2-2 | Substance No.2-3 |
| $\rightarrow ^3G^1_6 \rightarrow$ | | 0.3 | 0.1 | 0.3 | 0.5 |
| $G^1 \rightarrow$ | | 1 | 1 | 1 | 1 |
| Acute toxicity ($LD_{50}$, mg/kg) to mouse | | | | | |
| Intravenous | Male | >1300 | >1300 | >1300 | >1300 |
| | Female | " | " | " | " |
| Subcutaneous | Male | >5000 | >5000 | >5000 | >5000 |
| | Female | " | " | " | " |
| Intraperitoneal | Male | >5000 | >5000 | >5000 | >5000 |
| | Female | " | " | " | " |
| Oral | Male | >20000 | >20000 | >20000 | >20000 |
| | Female | " | " | " | " |
| Acute toxicity ($LD_{50}$, mg/kg) to rat | | | | | |
| Intravenous | Male | >600 | >600 | >600 | >600 |
| | Female | " | " | " | " |
| Subcutaneous | Male | >5000 | >5000 | >5000 | >5000 |
| | Female | " | " | " | " |
| Intraperitoneal | Male | >5000 | >5000 | >5000 | >5000 |
| | Female | " | " | " | " |
| Oral | Male | >20000 | >20000 | >20000 | >20000 |
| | Female | " | " | " | " |
| Antitumor activity (tumor growth inhibition, %) to transplanted sarcoma-180 cells (mice, in vivo) Route of administration daily dose rate | | | | | |
| intraperitoneal | 5 mg/kg[2] | 90 | 95 | 90 | 90 |
| intraperitoneal | 10 mg/kg[2] | 95 | 90 | 90 | 92 |
| intraperitoneal | 50 mg/kg[2] | 97 | 90 | 90 | 90 |
| Oral | 100 mg/kg[3] | 60 | 50 | 60 | 55 |
| Oral | 600 mg/kg[3] | 60 | 50 | 60 | 55 |
| Oral | 1000 mg/kg[3] | 70 | 55 | 60 | 60 |

Note:
[1] measured at 100 MHz, 100° C. in $D_2O$
[2] every other day; in total 10 times of administration
[3] every day; in total 20 times of administration As appreciated from the experimental results shown above, the present substance can be administered by way of oral and intraperitoneal administration.

One notable characteristic of the polysaccharides of the present invention is their lack of allergenicity because they do not contain proteins, resulting in a safe intravenation, etc. The correlation between the results of experiments on mammals and application to human cases is clearly shown in the literature (Akio HOSHI and Kazuo KURETANI, Farumashia, 9,464–468, 1973). Accordingly, in the case of oral administration for treatment of cancer of gastro-intestinal tract, such as esophagus cancer, stomach cancer, colon cancer and rectal cancer, cancer in the region of head and neck, breast cancer, lung cancer, malignant lymphoma and other tumors of adult patients, the normal daily dose rate, although varying depending on the number of times of administration, is preferably within the range of 15 mg/kg to 100 mg/kg, and in the case of injection, the normal daily dose rate is preferably not greater than 10 mg/kg.

When the substance is prepared into solid forms for oral administration, such as tablets, grains, powder, capsules, etc., the composition may contain a binder, inclusion agent, shaping agent, lubricant, disintegrator, wetting agent or other like adducts. The substance may be also formed into oral liquid preparations such as internal liquid medicines, shake mixtures, suspensions, emulsions, sirups, etc., or it may be in the form of a dry product which is redissolved before use. Such liquid preparations may contain the normally used types of additives or preservatives.

The preparations for injection may also contain an additive or additives such a stabilizer, buffering agent, preservative, isotonizing agent, etc., and they may be supplied in the form of ampoules containing a unit dose of the substance or containers containing multiple doses of the substance. The injection compositions may be prepared in the form of an aqueous solution, suspension solution, or emulsion in an oil or aqueous vehicle, and the active substance may be supplied in the form of powder which, when administered, is redissolved in a suitable vehicle, such as sterilized water not containing any pyrogenic substance.

As reviewed above, the polysaccharide substance according to the present invention exhibits a very excellent effect when orally administered as an antitumor agent. The present substance also gives immunopotentiation through the host and is effective for preventing side effects in chemotherapy or for raising sensitivity in radiotherapy. Further, the present substance is useful for preventing suppression of immunity or physical strength of the patients and for protecting the patient against viral or bacterial infection to which the patient is susceptible due to reduced immunity. Among other prominent effects provided by the present substance through its oral administration are improvement of liver function, remedy of intestinal disorders and promotion of urination.

The invention is now described in further detail by way of examples, but the scope of this invention is not limited to these examples.

EXAMPLE 1

CM-103 strain (F.R.I. Deposit No. 2414) of *Coriolus versicolor* (Fr.) Quél. was inoculated in a 200 ml conical flask containing 30 ml of a culture medium containing 5% of glucose, 0.2% of peptone, 0.3% of yeast extract, 0.1% of $KH_2PO_4$ and 0.1% of $MgSO_4.7H_2O$ and subjected to 10-day stationary culture at 25 to 27° C., and the mycelial mat grown on the surface of the culture medium was homogenized with an aqueous physiological saline solution, thereby preparing the seed culture.

20 liters of slurry of the seed culture were inoculated in 1,600 liters of a culture medium containing 10% glucose, 1.5% yeast extract, 0.1% $KH_2PO_4$ and 0.1% $MgSO_4.7H_2O$ in a $2M^3$ vertical fermenter and cultured at an aeration rate of 0.5 l/min per liter of the culture medium, an agitation rate of 150 r.p.m., and at a temperature of 26° C. for 7 days. The thus culture material was batched off in portions of about 500 liters, and each portion was dried by a double drum-type dryer to obtain approximately 30 kg of dry product. 100 g of this dry product were put into a 5-liter-capacity flask having an agitator together with 3 liters of water and maintained at an internal temperature of 95°±2° C. for 3 hours while continuing agitation, and then after cooling, the thus treated material was separated into the mycelial residue and the extract solution. Then the mycelial residue was washed with approximately 1 liter of water, and the washing was mixed with the extract solution. The mixed solution was approximately 3.5 liters.

The mycelial residue was mixed with 2 liters of 0.1N caustic soda solution and subjected to 2-hour extraction at 95°±2° C. in the same way as mentioned above, followed by cooling, neutralization with 2N hydrochloric acid and separation into the extract solution and the mycelial residue by means of suction filtration. After separation, the residue was washed with about 0.5 liter of water and the washing was mixed with the extract solution to obtain 2.2 liters of extract solution. The same treatment was performed with each 2 liters of 0.2N, 0.3N and 0.4N caustic soda solution by using each 0.5 liter of washing water, thereby obtaining in total approximately 7.2 liters of the extract solution.

The thus obtained extract solution was subjected to Amico's 2000 Bench Type Ultrafilter (with DM-5 membrane) under an operating pressure of 1.5 kg/cm² and at a temperature of 10° C. with agitation and cooling, thereby removing the low-molecular-weight substances and neutral salts therefrom, consequently obtaining 200 ml of a liquid.

The liquid was mixed with 160 g of ammonium sulfate and the thus produced precipitate was collected. This was then dissolved in water and desalted by using the above-mentioned Amicon's ultrafilter to obtain 190 ml of a liquid. This liquid was passed through a column of 1 cm in diameter and 100 cm in length packed with DEAE cellulose (OH form) to adsorb and remove the nitrogenous substance contained in the liquid, and water was passed through the column to obtain 20 liters of an eluate. The thus obtained eluate was concentrated to 180 ml by a rotary evaporator and then again passed through the DEAE cellulose column, and the resultant eluate was further concentrated by the rotary evaporator and freeze-dried to finally obtain 3.0 g of the object polysaccharide substance in a powdery form.

The properties of this substance were examined by following methods, and also animal tests such as described below were conducted on this substance.

(1) EXAMINATION OF PROPERTIES

Elementary Analysis

An elementary analysis of the present substance was carried out by Yanagimoto Manufacturing Company's Model CHN-CORDER MT-2 Analyzer.

Infrared absorption spectrum

An infrared absorption spectrum of the obtained powdery substance as a potassium bromide tablet is shown in FIG. 1. The tablet used in this method was prepared by mixing 1 g of KBr and about ⅓ to ½ spatulaful amount of the specimen according to a common method. Absorption was noted at 3600 to 3200 cm$^{-1}$, 2920 to 2900 cm$^{-1}$, 1660 to 1610 cm$^{-1}$, 1460 cm$^{-1}$, 1410 cm$^{-1}$, 1360 cm$^{-1}$, 1230 cm$^{-1}$, 1150 cm$^{-1}$, 1080 cm$^{-1}$, 1060 to 990 cm$^{-1}$, 925 cm$^{-1}$, 840 cm$^{-1}$, 755 cm$^{-1}$ and 705 cm$^{-1}$. Absorption at 840 cm$^{-1}$ is attributable to α-bonding of saccharides. This attests to the fact that the present substance is composed of α-bonded glucoside.

Specific rotatory Power

Optical rotatory power of the present substance was determined on an aqueous 0.25% solution thereof in a cell of 5 cm in optical path to the ray of Na-D line (589 nm) at 25° C., and shown as the value of specific rotatory power, $[\alpha]_D^{25}$.

NMR absorption spectrum

The NMR absorption spectrum was taken by using DSS as the internal standard and heavy water as the solvent. The numerical figures shown in the table are the values after correction under the supposition of Lorenz's curve of eliminating the influence of residual light water in the heavy water.

Molecular weight

The molecular weight of the present substance was measured by using the ultracentrifugal method. The results showed that the molecular weight of all the specimens tested is within the range of 5,000 to 300,000. For measurements, there were employed the sedimentation equilibrium and synthetic boundary pattern using an interference optical system. The experimental conditions were as follows: specimen concentration, 0.3%; solvent, 1/10M KCl; temperature, 25° C.; liquid column, 1.7 mm; speed, 22,000 r.p.m.; measuring time, 5 hours.

(2) SACCHARIDE COMPONENT OF GLUCOSIDE

The monosaccharide component of the present substance was analyzed in the following ways. Into a glass ampoule, 3 mg of a specimen of the present substance were placed, and after adding 10 ml of a 3% methanolic solution of hydrogen chloride thereto, the mixture was subjected to methanolysis at 100° C. for 16 hours, and after neutralizing the reaction mixture with silver carbonate, the neutralizate was filtered at room temperature. The filtrate was concentrated and evaporated to dryness and then dissolved in 0.5 ml of dry pyridine. The thus obtained solution was mixed with 0.2 ml of hexamethyldisilazane and 0.3 ml of trimethylchlorosilane, and the mixture was allowed to stand at room temperature for 30 minutes, for trimethylsilation. Upon completion thereof, the mixture was dissolved in chloroform, and after removing the excess reagent by washing with water, the solution was evaporated to dryness. The residue was dissolved in carbon tetrachloride and analyzed by gas chromatography. The results of the analysis showed that glucose accounted for more than 99% of the saccharide component of the present substance and other saccharides such as mannose, galactose, xylose, fucose and the like were scarce.

In order to know whether the glucose which is the principle constitutent of the saccharide portion of the present substance is D form or L form, the glucose was isolated from the hydrolyzate of the present substance by a column and its melting point was measured. It was 143° to 145° C. This glucose showed no drop of melting point when mixed and melted with a standard preparation of D-glucose. From this result, the glucose in the present substance was identified as D-glucose.

(3) PATTERN OF SACCHARIDE BONDING

The pattern of saccharide bonding in the present substance was determined according to Haworth's method. Into 10 ml of an aqueous 1N sodium hydroxide solution, 2 g of a specimen of the present substance were dissolved, and while maintaining the solution at 40° to 50° C. under a nitrogen stream and violent agitation, 20 ml of dimethylsulfuric acid and 40 ml of 30% sodium hydroxide solution were added dropwise over a period of several hours, and after allowing the mixture to stand overnight, it was subjected to the similar treatment with an equal amount of the methylating reagent. The reaction solution, after being neutralized, was dialyzed against running water and the dialyzate was concentrated under a reduced pressure and subjected to the above-mentioned methylation treatment three times, and after additional neutralization and dialysis, the mixture was evaporated to dryness under a reduced pressure. The residue was dissolved in 20 ml of a mixture of chloroform and methanol (10:1 by volume), and into the thus formed solution, a mixture of petroleum ether and diethyl ether (1:1 by volume) was added to precipitate the methylated product of the present substance. Then, about 20 mg of this methylated substance was hydrolyzed with 1N sulfuric acid at 100° C. for 16 hours, and the hydrolyzate was converted into alditol-acetate according to an ordinary method and the molar ratio was determined from the peak area on the gas chromatograph. For distinction between 2, 3, 6-Tri—O—Me—G and 2, 3, 4,-Tri—O—Me—G, 20 mg of the methylated substance was subjected to methanolysis at 100° C. for 16 hours in a sealed tube by using a 3% methanolic solution of hydrogen chloride. 2, 3, 4-Tri—O—Me—G was not detected in the gas chromatographic analysis of the methanolysis product. For confirmation, each of the decomposed products was identified on the gas chromatograph by using a standard preparation, while each hydrolyzate was isolated by using column liquid chromatography and either crystallized or converted into a crystalline derivative.

The properties, structural characteristics and antitumor activities of the thus obtained polysaccharide substances of the present invention are shown comprehensively in Table 6.

EXAMPLE 2

Each seed culture was prepared by the same procedures as in Example 1 from each of the following basidiomycetous fungal species belonging to the genus Coriolus in the following culture medium.

| Species | Strain |
|---|---|
| Coriolus consors(Berk.)Imaz. | CM-166(F.R.I. Deposit FERM-P No. 988) |
| Coriolus pargamenus(Fr.)Pat. | CM-161(F.R.I. Deposit FERM-P No. 2712) |
| Coriolus hirsutus(Fr.)Quel. | CM-151(F.R.I. Deposit FERM-P No. 2711) |

Recipe of the culture medium
3 g of peptone,
5 g of yeast extract,
0.1 g of potassium dihydrogen phosphate,
0.1 g of dipotassium hydrogen phosphate,
0.05 g of magnesium sulfate heptahydrate,
20 g of glucose,
10 g of malt extract and
1 liter of water, the pH of the culture medium being 6.0.

Each 200 ml of the above-mentioned culture medium was pipetted into 400 culture bottles (1-liter volume), and 1 ml of the seed culture was inoculated in the each culture medium followed by 25-day incubation at 25° to 30° C. and then drying to obtain 980 g of dry mycelia from Coriolus consors (Berk.) Imaz. CM-166, 1,200 g from Coriolus pargamenus (Fr.) Pat. CM-161 and 1,500 g from Coriolus hirsutus (Fr.) Quél. respectively.

Then, 100 g of the thus obtained dry mycelia from each seed culture and 2 liters of 0.4N caustic soda solution were placed in an extraction vessel equipped with a heating/cooling jacket and an agitator and subjected to 2-hour extraction under agitation by adjusting the jacket temperature at 90° to 95° C. After cooling the thus treated mixture to room temperature, an aqueous 2N hydrochloric acid solution was added to the mixture, and after adjusting the pH to 7, the mixture was separated into an extract solution and a mycelial residue by centrifugation.

Then the mycelial residue was mixed with 2 liters of 0.4N caustic soda solution and subjected to a similar 2-hour extraction at 90° to 95° C., followed by cooling, neutralization and centrifugal separation to obtain an extract solution and a mycelial residue. The latter was further subjected to a similar extraction operation for one hour with 0.4N caustic soda solution, then cooled, neutralized and centrifugally separated into a extract solution and a mycelial residue, the latter being once again subjected to 1-hour extraction with 0.4N caustic soda solution, cooling, neutralization and centrifugal separation.

The total four runs of extraction operations gave approximately 8.4 liters of the whole extract solution. This extract solution was concentrated to 3 liters, then put into a cellulose tube for dialysis (Visking tube by Union Carbide) and subjected to 6-day running water dialysis with tap water, and the solution remaining in the tube was concentrated to obtain 190 ml of liquid.

The thus concentrated liquid was then mixed with 160 g of ammonium sulfate and the thus produced precipitate was collected, dissolved in water and further subjected to 6-day dialysis by using the Visking tube, and then the solution remaining in the tube was concentrated to 410 ml.

This concentrated liquid was treated by the same manner as EXAMPLE 1, that is, passed through a DEAE cellulose column to adsorb and remove the nitrogenous component from the liquid and the resultant solution was concentrated by a rotary evaporator and dried, thereby consequently obtaining the object polysaccharide substance in dry powdery form.

The amount of the polysaccharide substance obtained from each seed culture of the specified fungal species was as follows.

| Among(g) | Species | Strain | Deposit No. |
|---|---|---|---|
| 6.0 | Coriolus consors(Berk.)Imaz. | CM-166 | FERM-P No. 2414 |
| 6.5 | Coriolus pargamenus(Fr.)Pat. | CM-161 | FERM-P No. 2712 |
| 5.5 | Coriolus hirsutus(Fr.)Quel. | CM-151 | FERM-P No. 2711 |

For reference, the polysaccharide substances are referred to as 2-1, 2-2 and 2-3 in the above-mentioned order.

The properties of the obtained substances, results of animal tests, infrared absorption spectra, NMR absorption spectra, molecular weight, specific rotatory power of the saccharide component and pattern of saccharide bonding are shown in Table 7 together with those of the product of EXAMPLE 1.

EXAMPLE 3

The extract solution (7.2 liters) of *Coriolus versicolor* (Fr.) Quél. of Example 1 was subjected to ultrafiltration at 10° C. in an ultrafilter (Amicon's 2000 Bench Type Ultrafilter (with DM-5 membrane)) provided with a membrane which only allows the pass of the substances of molecular weight smaller than 5,000 to leave a solution only containing the substances not smaller than 5,000 in molecular weight in the ultrafilter, under a pressure. Operation of ultrafiltration was carried out three times while changing the pressure each time. The pressure and the time period taken in each run of ultrafultration are shown in Table 7 together with the amount of the remained solution containing only the molecules larger than 5,000 in molecular weight.

The solution left in the ultrafilter was saturated with ammonium sulfate at room temperature by adding crystals of ammonium sulfate into the solution at a rate of 90% by weight to volume to salting the polysaccharide out from the solution. The thus deposited polysaccharide was dissolved into water.

The aqueous solution of the polysaccharide obtained as above was subjected to ultrafiltration in the same ultrafilter provided with the same membrane as mentioned above to remove ammonium sulfate which was contained in the salted-out polysaccharide.

The aqueous solution left in the ultrafilter was subjected to column chromatography by pouring into the solution into a column packed with diethylaminoethyl-cellulose (DEAE-cellulose) to absorb nitrogenous materials contaminated by the polysaccharide. The effluent solution deprived of the nitrogenous materials was collected, condensed under a reduced pressure and then dried. The technological process conditions are also shown in Table 8 together with the total yield of the process. The properties, structural characteristics and anti-tumor activities of the thus obtained polysaccharide are shown comprehensively in Table 11.

TABLE 8

| | Technological Process Conditions and Parameters | | | | | | | | | |
|---|---|---|---|---|---|---|---|---|---|---|
| | First Ultrafiltration | | | Salting out | | Second Ultrafiltration | | | Column chromato. Solution | Condensation | Drying |
| Run number | Pressure (kg/cm$^2$) | Time (hour) | Remained solution (ml) | (NH$_4$)$_2$SO$_4$ to solution (g/ml) | Dissolution (g/ml)* | Pressure (kg/cm$^2$) | Time (hour) | Remained solution (g/ml)** | passed column (liter)*** | Condensate (ml) | Dried Product (g) |
| 1 | 0.5 | 2.5 | 380 | 342/380 | 8.4/280 | 0.5 | 1.5 | 3/100 | 20 | 180 | 4.2 |
| 2 | 0.5 | 2.5 | 380 | 342/380 | 8.4/280 | 1.5 | 1.5 | 3/100 | 20 | 180 | 4.2 |
| 3 | 0.5 | 2.5 | 380 | 342/380 | 8.4/84 | 1.5 | 4.5 | 10/100 | 20 | 180 | 4.2 |
| 4 | 0.5 | 2.5 | 380 | 342/380 | 8.4/280 | 5.0 | 1 | 3/100 | 20 | 180 | 4.2 |
| 5 | 3.0 | 2 | 150 | 135/150 | 8.4/280 | 0.5 | 1.5 | 3/100 | 20 | 180 | 4.2 |
| 6 | 3.0 | 2 | 150 | 135/150 | 8.4/280 | 1.5 | 1.5 | 3/100 | 20 | 180 | 4.2 |
| 7 | 3.0 | 2 | 150 | 135/150 | 8.4/84 | 1.5 | 4.5 | 10/100 | 20 | 180 | 4.2 |
| 8 | 3.0 | 2 | 150 | 135/150 | 8.4/280 | 5.0 | 1 | 3/100 | 20 | 180 | 4.2 |
| 9 | 5.0 | 2.5 | 110 | 99/110 | 8.4/280 | 0.5 | 1.5 | 3/100 | 20 | 180 | 4.2 |
| 10 | 5.0 | 2.5 | 110 | 99/110 | 8.4/280 | 1.5 | 1.5 | 3/100 | 20 | 180 | 4.2 |
| 11 | 5.0 | 2.5 | 110 | 99/110 | 8.4/84 | 1.5 | 4.5 | 10/100 | 20 | 180 | 4.2 |
| 12 | 5.0 | 2.5 | 110 | 99/110 | 8.4/280 | 5.0 | 1 | 3/100 | 20 | 180 | 4.2 |

Notes:
*Salted-out substance (g) was dissolved in distilled water (ml)
**Substance (g) contained in unit amount of the solution remained in the ultrafilter.
***Solution which passed the column plus the washings of the column with distilled water.

EXAMPLE 4

The extract solution (7.2 liters) of *Coriolus versicolor* (Fr. Quél. of Example 1 was subjected to reverse osmosis at 10° C. in an apparatus for reverse osmosis provided with a membrane which only allows the pass of the substances smaller than 5,000 in molecular weight. Operation of reverse osmosis was repeated three times while changing the pressure in osmosis and time period shown in Table 9 together with the amount of the solution deprived of the substance smaller than 5,000 in molecular weight.

The solution left in the reverse osmosis was saturated with ammonium sulfate at room temperature by adding crystals of ammonium sulfate into the solution at a rate of 90% by weight to volume for salting the polysaccharide out from the solution. The thus deposited polysaccharide was dissolved into water.

The aqueous solution of the polysaccharide obtained as above was subjected to ultrafiltration in the same ultrafilter provided with the same membrane as Example 3 to remove ammonium sulfate which was contained in the salted-out polysaccharide.

The aqueous solution left in the ultrafilter was subjected to column chromatography by pouring the solution into a column packed with DEAE-cellulose to absorb nitrogenous materials contaminated by the polysaccharide. The effluent solution deprived of the nitrogenous materials was collected, condensed under a reduced pressure and then dried. The technological process conditions are also shown in Table 9 together with the total yield of the process.

The properties, structural characteristics and antitumor activities of the thus obtained polysaccharide are shown comprehensively in Table 12.

absorb nitrogenous materials contaminated by the polysaccharide. The effluent solution deprived of the nitrogenous materials was collected, condensed under a reduced pressure and then dried. The technological process conditions are also shown in Table 10 together with the total yield of the process.

The properties, structural characteristics and antitumor activities of the thus obtained polysaccharide are shown comprehensively in Table 12.

EXAMPLE 6

The extract solution (7.2 liters) of *Coriolus versicolor* (Fr.) Quél. of Example 1 was subjected to reverse osmosis at a temperature of 10° C. in an apparatus for reverse

TABLE 9

Technological Processs Conditions and Parameters

| Run number | Reverse Osmosis Pressure ($kg/cm^2$) | Reverse Osmosis Time (hr) | Remained solution (ml) | Salting out $(NH_4)_2SO_4$ to solution (g/ml) | Dissolution (g/ml) | Ultrafiltration Pressure ($kg/cm^2$) | Ultrafiltration Time (hr) | Remained solution (g/ml) | Column Chromato. Solution passed column (liter) | Condensation Condensate (ml) | Drying Dried Product (gram) |
|---|---|---|---|---|---|---|---|---|---|---|---|
| 1 | 20 | 4.5 | 180 | 162/180 | 8.4/280 | 0.5 | 1.5 | 3/100 | 20 | 180 | 4.2 |
| 2 | 20 | 4.5 | 180 | 162/180 | 8.4/280 | 1.5 | 1.5 | 3/100 | 20 | 180 | 4.2 |
| 3 | 20 | 4.5 | 180 | 162/180 | 8.4/280 | 1.5 | 4.5 | 10/100 | 20 | 180 | 4.2 |
| 4 | 20 | 4.5 | 180 | 162/180 | 8.4/280 | 5.0 | 1 | 3/100 | 20 | 180 | 4.2 |
| 5 | 29 | 5 | 150 | 135/150 | 8.4/280 | 0.5 | 1.5 | 3/100 | 20 | 180 | 4.2 |
| 6 | 29 | 5 | 150 | 135/150 | 8.4/280 | 1.5 | 1.5 | 3/100 | 20 | 180 | 4.2 |
| 7 | 29 | 5 | 150 | 135/150 | 8.4/280 | 1.5 | 4.5 | 10/100 | 20 | 180 | 4.2 |
| 8 | 29 | 5 | 150 | 135/150 | 8.4/280 | 5.0 | 1 | 3/100 | 20 | 180 | 4.2 |
| 9 | 35 | 5 | 110 | 99/110 | 8.4/280 | 0.5 | 1.5 | 3/100 | 20 | 180 | 4.2 |
| 10 | 35 | 5 | 110 | 99/110 | 8.4/280 | 1.5 | 1.5 | 3/100 | 20 | 180 | 4.2 |
| 11 | 35 | 5 | 110 | 99/110 | 8.4/280 | 1.5 | 4.5 | 10/100 | 20 | 180 | 4.2 |
| 12 | 35 | 5 | 110 | 99/110 | 8.4/280 | 5.0 | 1 | 3/100 | 20 | 180 | 4.2 |

EXAMPLE 5

The extract solution (7.2 liters) of *Coriolus versicolor* (Fr.) Quél. of Example 1 was subjected to ultrafiltration at 10° C. by charging the solution into an ultrafilter (Amicon's 2000 Bench Type Ultrafilter (with DM-5 membrane)) provided with a membrane which only allows the pass of the substances of molecular weight smaller than 5,000 to leave a solution only containing the molecules not smaller than 5,000 in molecular weight in the ultrafilter, under a pressure. Operation of ultrafiltration was carried out three times while changing the pressure each time. The pressure and the time period taken in each run of ultrafiltration are shown in Table 9 together with the amount of the remained solution containing only the molecules larger than 5,000 in molecular weight.

The solution left in the ultrafilter was saturated with ammonium sulfate at room temperature by adding crystals of ammonium sulfate into the solution at a rate of 90% by weight to volume for salting the polysaccharide out from the solution. The thus deposited polysaccharide was dissolved into water.

The aqueous solution of the polysaccharide obtained as above was subjected to ultrafiltration in the same ultrafilter provided with the same membrane to remove ammonium sulfate which was contained in the salted-out polysaccharide.

The aqueous solution left in the ultrafilter was subjected to column chromatography by pouring the solution into a column packed with DEAE-cellulose to osmosis provided with a membrane which only allows the pass of the substances smaller than 5,000 in molecular weight. Operation of reverse osmosis was repeated three times while changing the pressure in osmosis and time period shown in Table 10 together with the amount of the solution deprived of the molecules smaller than 5,000 in molecular weight.

The solution left in the reverse osmosis was saturated with ammonium sulfate at room temperature by adding crystals of ammonium sulfate into the solution at a rate of 90% by weight to volume for salting the polysaccharide out from the solution. The thus deposited polysaccharide was dissolved into water.

The aqueous solution of the polysaccharide obtained as above was subjected to ultrafiltration in the same ultrafilter provided with the same membrane as Example 5 to remove ammonium sulfate which was contained in the salted-out polysaccharide.

The aqueous solution left in the ultrafilter was subjected to column chromatography by pouring the solution into a column packed with DEAE-cellulose to absorb nitrogenous materials contaminated by the polysaccharide. The effluent solution deprived of the nitrogenous materials was collected, condensed under a reduced pressure and then dried. The technological process conditions are also shown in Table 11 together with the total yield of the process.

The properties, structural characteristics and antitumor activities of the thus obtained polysaccharide are shown comprehensively in Table 12.

TABLE 10

Technological Process Conditions and Parameters

| Run number | First Ultrafiltration Pressure (kg/cm$^2$) | Time (hr) | Remained solution (ml) | Salting out (NH$_4$)$_2$SO$_4$ to solution (g/ml) | Dissolution (g/ml)* | Second Ultrafiltration Pressure (kg/cm$^2$) | Time (hr) | Remained solution (g/ml)** | Column chromato. Solution passed column*** (liter) | Condensation Condensate (ml) | Drying Dried Product (gram) |
|---|---|---|---|---|---|---|---|---|---|---|---|
| 1 | 0.5 | 1.5 | 840 | 756/840 | 8.4/280 | 0.5 | 1.5 | 3/100 | 20 | 180 | 4.2 |
| 2 | 0.5 | 1.5 | 840 | 756/840 | 8.4/280 | 1.5 | 1.5 | 3/100 | 20 | 180 | 4.2 |

Notes:
*Salted-out substance (g) was dissolved in distilled water (ml)
**Substance (g) contained in unit amount of the solution remained in the ultrafilter.
***Solution which passed the column plus the washings of the column with distilled water.

TABLE 11

Technological Process Conditions and Parameters

| Run number | Reverse Osmosis Pressure (kg/cm$^2$) | Time (hr) | Remained solution (ml) | Salting out (NH$_4$)$_2$SO$_4$ to solution (g/ml) | Dissolution (g/ml)* | Ultrafiltration Pressure (kg/cm$^2$) | Time (hr) | Remained solution (g/ml)** | Column chromato. Solution passed column (liter)*** | Condensation Condensate (ml) | Drying Dried Product (gram) |
|---|---|---|---|---|---|---|---|---|---|---|---|
| 1 | 20 | 3.0 | 300 | 270/300 | 8.4/280 | 0.5 | 1.5 | 3/100 | 20 | 180 | 4.2 |
| 2 | 20 | 3.0 | 300 | 720/800 | 8.4/280 | 1.5 | 1.5 | 3/100 | 20 | 180 | 4.2 |

Notes:
*Salted-out substance (g) was dissolved in distilled water (ml)
**Substance (g) contained in unit amount of the solution remained in the ultrafilter.
***Solution which passed the column plus the washings of the column with distilled water.

TABLE 12

| Example No. | 3 | 4 | 5 | 6 |
|---|---|---|---|---|
| F.R.I. Deposit No. FERM-P | No. 2412 | No. 2414 | No. 2414 | No. 2414 |
| Strain No. | CM-103 | CM-103 | CM-103 | CM-103 |
| Extraction Method | Hot water-alkali | Hot water-alkali | Hot water-alkali | Hot water-alkali |
| Molecular weight ($\times 10^4$) | 0.6–28 | 0.5–28 | 0.5–28 | 0.6–27 |
| Average mol. wt. ($\times 10^4$) | 7.2 | 7.1 | 7.3 | 7.2 |
| Color reaction (saccharide) | | | | |
| $\alpha$-naphthol-sulfuric acid reaction | Purple | Purple | Purple | Purple |
| Indol-sul. acid reaction | Brown | Brown | Brown | Brown |
| Anthrone-sul. acid reaction | Greenish blue | Greenish blue | Greenish blue | Greenish blue |
| Phenol-sul. acid reaction | Brown | Brown | Brown | Brown |
| Tryptophane-sul. acid reaction | Purplish brown | Purplish brown | Purplish brown | Purplish brown |
| pH Value | 6.7 | 6.8 | 6.8 | 6.7 |
| Specific rotary power $[\alpha]_D^{25}$ | 170 | 160 | 170 | 170 |
| Elemental analysis | | | | |
| C(%) | 44.89 | 44.76 | 44.85 | 44.80 |
| H(%) | 6.38 | 6.29 | 6.35 | 6.33 |
| N(%) | 0 | 0 | 0 | 0 |
| NMR absorption spectra Absorption positions (ppm) (measured at 100 MHz, 100° C. in D$_2$O) | | | | |
| 0.9–2.0 ppm | Absent | Absent | Absent | Absent |
| 3.6–3.9 ppm | Present | Present | Present | Present |
| 5.0 ± 0.1 ppm | Present | Present | Present | Present |
| 5.4 ± 0.1 ppm | Present | Present | Present | Present |
| Main sugar constituent | D-glucose | D-glucose | D-glucose | D-glucose |
| Infrared absorption spectra | | | | |
| 3600–3200 cm$^{-1}$ | Present | Present | Present | Present |
| 2920–2900 cm$^{-1}$ | Present | Present | Present | Present |
| 1660–1610 cm$^{-1}$ | Present | Present | Present | Present |
| 1460,1410,1360,1230 cm$^{-1}$ | Present | Present | Present | Present |
| 890 cm$^{-1}$ | Absent | Absent | Absent | Absent |
| 840 cm$^{-1}$ | Present | Present | Present | Present |
| Saccharide analysis (pattern of bonding) | | | | |
| $\rightarrow^4G^1\rightarrow$ | 5.6 | 5.7 | 5.5 | 5.6 |
| $\rightarrow^3G^1\rightarrow$ | 1.1 | 1.2 | 1.1 | 1.2 |
| $\rightarrow^4G^1_6\rightarrow$ | 1.1 | 1.1 | 1.0 | 0.9 |

TABLE 12-continued

| Example No. | | 3 | 4 | 5 | 6 |
|---|---|---|---|---|---|
| $\rightarrow^4G^1_3\rightarrow$ <br> $\uparrow$ | | 2.1 | 2.0 | 2.2 | 2.0 |
| $\rightarrow^3G^1_6\rightarrow$ <br> $\uparrow$ | | 0.4 | 0.3 | 0.3 | 0.5 |
| $G^1\rightarrow$ | | 1 | 1 | 1 | 1 |
| Acute toxicity (mice, LD$_{50}$ (mg/kg)) | | | | | |
| Intravenous | Male | >1300 | >1300 | >1300 | >1300 |
| | Female | >1300 | >1300 | >1300 | >1300 |
| Subcutaneous | Male | >5000 | >5000 | >5000 | >5000 |
| | Female | >5000 | >5000 | >5000 | >5000 |
| Intraperitoneal | Male | >5000 | >5000 | >5000 | >5000 |
| | Female | >5000 | >5000 | >5000 | >5000 |
| Oral | Male | >20000 | >20000 | >20000 | >20000 |
| | Female | >20000 | >20000 | >20000 | >20000 |
| (Rats, LD$_{50}$ (mg/kg)) | | | | | |
| Intravenous | Male | >600 | >600 | >600 | >600 |
| | Female | >600 | >600 | >600 | >600 |
| Subcutaneous | Male | >5000 | >5000 | >5000 | >5000 |
| | Female | >5000 | >5000 | >5000 | >5000 |
| Intraperitoneal | Male | >5000 | >5000 | >5000 | >5000 |
| | Female | >5000 | >5000 | >5000 | >5000 |
| Oral | Male | >20000 | >20000 | >20000 | >20000 |
| | Female | >20000 | >20000 | >20000 | >20000 |
| Antitumor (growth inhibition, %) (mice, in vivo) Route of administration Daily dose rate | | | | | |
| intraperitoneal | 5 mg/kg | 90 | 90 | 90 | 90 |
| intraperitoneal | 10 mg/kg | 95 | 95 | 95 | 95 |
| intraperitoneal | 50 mg/kg | 97 | 97 | 95 | 97 |
| Oral | 600 mg/kg | 65 | 65 | 65 | 65 |
| Oral | 1000 mg/kg | 70 | 70 | 70 | 70 |

Note: Antitumour activity of the present substance:

(i) Antitumour activity to solid-type Sarcoma-180 tumour:

Cells of Sarcoma-180 proliferated by the ordinary method were transplanted to the abdominal cavity of 4 groups of ICR-JCL mice at $1 \times 10^6$ cells/animal, and after 24 hours of transplantation, to each of 3 groups of the mice, each of the present substances was intraperitoneally administered once every other day for total 10 times at the respective dosages of 5, 10 and 50 mg/kg per time. After 25 days of the transplantation, the tumours appearing in all the mice were extirpated, and the average weight of tumours of each administered group (T) were compared with the average weight of tumours of the fourth group of mice not administered with the present substance (C) according to the following formula, and the results were expressed by the tumour-inhibiting extent:

$$\text{Tumour-inhibiting extent}(\%) = \left(1 - \frac{T}{C}\right) \times 100.$$

Furthermore, in another test, the present substance was orally administered, in stead of intraperitoneal injection, to the two groups of tumour-transplanted mice at the respective dosages of 600 and 1000 mg/kg/time, respectively, and the tumour-inhibition was examined in the same manner as above.

What is claimed is:

1. A polysaccharide having a molecular weight of from 5,000 to 300,000 as determined by ultracentrifugation, giving color reactions characteristic of saccharides in α-naphthol-sulfuric acid reaction, indole-sulfuric acid reaction, phenol-sulfuric acid reaction, and tryptophane-sulfuric acid reaction, containing 43.5 to 45.3% by weight of carbon, 5.7 to 6.7% by weight of hydrogen and the balance of oxygen and being free of nitrogen, the saccharide units of said polysaccharide being composed principally of D-glucose bonded together entirely by α-bonding and having a structure in which $\rightarrow^4G^1\rightarrow$ is within the range of 3.5 to 8.5, $\rightarrow^3G^1\rightarrow$ is less than 2, $\rightarrow^4G_6^1\rightarrow$ is within the range of 0.5 to 2.0, $\rightarrow^4G_3^1\rightarrow$ is within the range of 0.1 to 2.5, and $\rightarrow^3G_6^1\rightarrow$ is less than 0.8 when the non-reducing end-group ($G^1\rightarrow$) of monosaccharide as determined in a methylation-hydrolysis test according to Haworth's method is indexed as 1, the specific rotation $[\alpha]_D^{25}$ of said polysaccharide being +70° to +180°, said polysaccharide showing a specific absorption at 840 cm$^{-1}$ in its infrared absorption spectrum and showing absorptions at 3.7±0.1, 3.8±0.1, 5.0±0.1, and 5.4±0.1 ppm but not showing any absorptions in the range of 4.4 to 4.9 ppm in its nuclear magnetic resonance absorption spectrum, and said polysaccharide being soluble in water but insoluble in pyridine, chloroform, and hexane.

2. The polysaccharide according to claim 1, wherein the average molecular weight of said polysaccharide is within the range of from 10,000 to 100,000.

3. A pharmaceutical composition in a unit dosage form comprising a therapeutically effective dosage for treating mammalian gastro-intestinal cancer of a polysaccharide as an active ingredient and at least one pharmaceutically acceptable substance selected from the group consisting of galactose, heavy magnesium oxide, starch, monosaccharides, crystalline cellulose, poly(vinyl alcohol), non-ionic surfactants, and physiological saline solutions, said polysaccharide having a molecular weight of from 5,000 to 300,000 as determined by ultracentrifugation, giving color reactions characteristic of saccharides in α-naphthol-sulfuric acid reaction, indole-sulfuric acid reaction, phenol-sulfuric acid reaction, and tryptophane-sulfuric acid reaction, containing 43.5 to 45.3% by weight of carbon, 5.7 to 6.7% by weight of hydrogen and the balance of oxygen and free of nitrogen, the saccharide units of said polysaccharide being composed principally of D-glucose bonded together entirely by α-bonding and having a structure in which →$^4$G$^1$→ is within the range of 3.5 to 8.5, →$^3$G$^1$→ is less than 2, →$^4$G$_6^1$→ is within the range of 0.5 to 2.0, →$^4$G$_3^1$→ is within the range of 0.1 to 2.5 and →$^3$G$_6^1$→ is less than 0.8 when the non-reducing endgroup (G$^1$→) of monosaccharide as determined in a methylation-hydrolysis test according to Haworth's method is indexed as 1, the specific rotation $[\alpha]_D^{25}$ of said polysaccharide being +70° to +180°, said polysaccharide showing a specific absorption at 840 cm$^{-1}$ in its infrared absorption spectrum and showing absorptions at 3.7±0.1, 3.8±0.1, 5.0±0.1, and 5.4±0.1 ppm but not showing any absorptions in the range of 4.4 to 4.9 ppm in its nuclear magnetic resonance absorption spectrum, and said polysaccharide being soluble in water but not soluble in pyridine, chloroform, and hexane.

4. The pharmaceutical composition according to claim 3, wherein the average molecular weight of said polysaccharide is within the range of from 10,000 to 100,000.

5. A method of treating mammalian gastro-intestinal cancer, comprising the step of administering to a mammal bearing said gastrointestinal cancer a therapeutically effective amount of an antitumor agent containing a polysaccharide as an active ingredient, said polysaccharide having a molecular weight of from 5,000 to 300,000 as determined by ultracentrifugation, giving color reactions characteristic of saccharides in α-naphthol-sulfuric acid reaction, indole-sulfuric acid reaction, phenol-sulfuric acid reaction, and tryptophane-sulfuric acid reaction, containing 43.5 to 45.3% by weight of carbon, 5.7 to 6.7% by weight of hydrogen and the balance of oxygen and being free of nitrogen, the saccharide units of said polysaccharide being composed principally of D-glucose bonded together entirely by α-bonding and having a structure in which →$^4$G$^1$→ is within the range of 3.5 to 8.5, →$^3$G$^1$→ is less than 2, →$^4$G$_6^1$→ is within the range of 0.5 to 2.0, →$^4$G$_3^1$→ is within the range of 0.1 to 2.5 and →$^3$G$_6^1$→ is less than 0.8 when the non-reducing endgroup (G$^1$→) of monosaccharide as determined in methylation-hydrolysis test according to Haworth's method is indexed as 1, the specific rotation $[\alpha]_D^{25}$ of said polysaccharide being +70° to +180°, said polysaccharide showing a specific absorption at 840 cm$^{-1}$ in its infrared absorption spectrum and showing absorptions at 3.7±0.1, 3.8±0.1, 5.0±0.1, and 5.4±0.1 ppm but not showing any absorptions in the range of 4.4 to 4.9 ppm in its nuclear magnetic resonance absorption spectrum, and said polysaccharide being soluble in water but insoluble in pyridine, chloroform, and hexane.

6. The method according to claim 5, wherein said gastro-intestinal cancer is selected from the group consisting of gastric cancer, colonic cancer and esophageal cancer.

7. The method according to claim 5, wherein the average molecular weight of said polysaccharide is within the range of from 10,000 to 100,000.

8. A polysaccharide having a molecular weight of from 5,000 to 300,000 as determined by ultracentrifugation, giving color reactions characteristic of saccharides in α-naphthol-sulfuric acid reaction, indole-sulfuric acid reaction, phenol-sulfuric acid reaction, and tryptophane-sulfuric acid reaction, containing 43.5 to 45.3% weight of carbon, 5.7 to 6.7% by weight of hydrogen and the balance of oxygen and being free of nitrogen, the saccharide units of said polysaccharide being composed principally of D-glucose bonded together entirely by α-bonding and having a structure in which →$^4$G$^1$→ is within the range of 3.5 to 8.5, →$^3$G$^1$→ is less than 2, →$^4$G$_6^1$→ is within the range of 0.5 to 2.0, →$^4$G$_3^1$→ is within the range of 0.1 to 2.5 and →$^3$G$_6^1$→ is less than 0.8 when the non-reducing endgroup (G$^1$→) of monosaccharide as determined in methylation-hydrolysis test according to Haworth's method is indexed as 1, the specific rotatory power $[\alpha]_D^{25}$ of said polysaccharide being +70° to +180°, said polysaccharide showing a specific absorption at 840 cm$^{-1}$ in its infrared absorption spectrum and showing absorptions at 3.7±0,1, 3.8±0.1, 5.0±0.1, and 5.4±0.1 ppm but not showing any absorptions in the range of 4.4 to 4.9 ppm in its nuclear magnetic resonance spectrum, and said polysaccharide being soluble in water but insoluble in pyridine, chloroform, and hexane, produced by the process comprising the steps of, extracting mycelia, fruit bodies of a basidiomycetous fungus selected from the group consisting of *Coriolus versicolor* (Fr.) Quél., *Coriolus Consors* (Berk.) Imaz., *Coriolus hirsutus* Fr.) Quél. and *Coriolus pargamenus* (Fr.) Pat. or mixtures thereof with an aqueous solvent selected from the group consisting of water, an aqueous dilute acid solution, an aqueous 0.005 to 2N solution of potassium- or sodium hydroxide, and an aqueous dilute solution of an organic solvent, saturating the thus-obtained extract solution with ammonium sulfate after removing the low-molecular weight substances with molecular weight of lower than 5,000 contained therein by ultrafiltration, reverse osmosis or a combination thereof, collecting the resultant precipitate, dissolving said precipitate in water, desalting the thus-obtained solution of said precipitate, passing the thus-desalted solution through a column packed with an ion exchanger, thereby absorbing and removing the nitrogenous substance contained therein, concentrating the thus-obtained solution, and drying the thus-obtained concentrate to obtain said polysaccharide.

9. The polysaccharide produced by the process according to claim 8, wherein said extraction is carried out by first extracting the fungus or cultured material thereof with water or a dilute aqueous alkali solution and further performing the extraction stepwise with the alkali solutions with successively raised concentration.

10. An antitumor agent comprising a therapeutically effective amount of a polysaccharide as an active ingredient and at least one pharmaceutically acceptable substance selected from the group consisting of galactose, heavy magnesium oxide, starch, monosaccharides, crystalline cellulose, poly(vinyl alcohol), non-ionic surfactants and physiological saline solutions, said polysaccharide having a molecular weight of from 5,000 to 300,000 as determined by ultracentrifugation, giving color reactions characteristic of saccharides in α-naphtol-sulfuric acid reaction, indole-sulfuric acid reaction, phenol-sulfuric acid reaction, and tryptophane-sulfuric acid reaction, containing 43.5 to 45.3% by weight of carbon, 5.7 to 6.7% by weight of hydrogen and the balance of oxygen and being free of nitrogen, the saccharide units of said polysaccharide being composed principally of D-glucose bonded together entirely by α-bonding and having a structure in which $\rightarrow^4G^1\rightarrow$ is within the range of 3.5 to 8.5, $\rightarrow^3G_6^1\rightarrow$ is less than 2, $\rightarrow^4G_6^1\rightarrow$ is within the range of 0.5 to 2.0, $\rightarrow^4G_3^1\rightarrow$ is within the range of 0.1 to 2.5 and $\rightarrow^3G_6^1\rightarrow$ is less than 0.8 when the non-reducing endgroup $(G^1\rightarrow)$ of monosaccharide as determined in methylation-hydrolysis test according to Haworth's method is indexed as 1, the specific rotation $[\alpha]_D^{25}$ of said polysaccharide being +70° to +180°, said polysaccharide showing a specific absorption at 840 cm$^{-1}$ in its infrared absorption spectrum and showing absorptions at 3.7±0.1, 3.8±0.1, 5.0±0.1, and 5.4±0.1 ppm but not showing any absorptions in the range of 4.4 to 4.9 ppm in its nuclear magnetic resonance absorption spectrum, and said polysaccharide being soluble in water but insoluble in pyridine, chloroform, and hexane.

11. The antitumor agent according to claim 10, wherein the average molecular weight of said polysaccharide is within the range of from 10,000 to 100,000.

* * * * *